(12) United States Patent
Chang et al.

(10) Patent No.: US 8,980,269 B2
(45) Date of Patent: Mar. 17, 2015

(54) G-PROTEIN COUPLED RECEPTOR-ASSOCIATED SORTING PROTEIN 1 AS A CANCER BIOMARKER

(71) Applicant: Temple University of the Commonwealth System of Higher Education, Philadelphia, PA (US)

(72) Inventors: Frank N. Chang, Dresher, PA (US); George P. Tuszynski, Pittsgrove, NJ (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 13/800,741

(22) Filed: Mar. 13, 2013

(65) Prior Publication Data

US 2013/0183317 A1 Jul. 18, 2013

Related U.S. Application Data (63) Continuation-in-part of application No. 13/464,174, filed on May 4, 2012, now Pat. No. 8,420,333, which is a continuation-in-part of application No. 13/384,014, filed as application No. PCT/US2010/041813 on Jul. 13, 2010.

(60) Provisional application No. 61/225,254, filed on Jul. 14, 2009.

(51) Int. Cl.
| | |
|---|---|
| *A61K 39/00* | (2006.01) |
| *A61K 39/395* | (2006.01) |
| *A61K 49/00* | (2006.01) |
| *A01N 61/00* | (2006.01) |
| *G01N 33/68* | (2006.01) |
| *G01N 33/574* | (2006.01) |
| *C12Q 1/68* | (2006.01) |

(52) U.S. Cl.
CPC ...... *G01N 33/6893* (2013.01); *G01N 33/57407* (2013.01); *G01N 33/57415* (2013.01); *G01N 33/57423* (2013.01); *G01N 33/57438* (2013.01); *C12Q 1/6886* (2013.01); *G01N 2800/56* (2013.01); *C12Q 2600/158* (2013.01)
USPC ....... 424/139.1; 424/9.1; 424/9.2; 424/130.1; 424/138.1; 514/1; 514/19.2; 514/19.3; 514/19.4

(58) Field of Classification Search
CPC ......... G01N 1/00; G01N 33/00; G01N 33/48; G01N 33/50; G01N 33/574; G01N 33/57407; G01N 33/57415; C07K 1/00; C07K 16/00; C07K 16/18; C07K 16/28; C07K 16/30; C07K 2316/00; C07K 2317/00; C07K 2317/34; C07K 7/00
USPC .................. 424/9.1, 9.2, 130.1, 138.1, 139.1; 514/1, 19.2, 19.3, 19.4
See application file for complete search history.

(56) References Cited

U.S. PATENT DOCUMENTS

| | | |
|---|---|---|
| 6,939,424 B1 | 9/2005 | Takala et al. |
| 7,326,326 B2 | 2/2008 | Chang et al. |
| 2004/0142862 A1 | 7/2004 | Whistler et al. |
| 2006/0019256 A1 * | 1/2006 | Clarke et al. ................. 435/6 |
| 2006/0266715 A1 | 11/2006 | Loewy |
| 2009/0023149 A1 | 1/2009 | Knudsen |
| 2009/0234202 A1 | 9/2009 | Goix et al. |
| 2011/0031122 A1 | 2/2011 | Chang et al. |
| 2011/0287450 A1 | 11/2011 | Bottaro et al. |
| 2012/0039811 A1 | 2/2012 | Admon et al. |

FOREIGN PATENT DOCUMENTS

| | | |
|---|---|---|
| WO | WO 01/65262 A2 | 9/2001 |
| WO | WO 03/031942 A1 | 4/2003 |
| WO | WO 03/056341 A2 | 7/2003 |
| WO | WO-2004052290 | 6/2004 |
| WO | WO-2005118856 | 12/2005 |
| WO | WO-2006125195 | 11/2006 |
| WO | WO 2008/031064 A1 | 3/2008 |
| WO | WO-2008079269 | 7/2008 |
| WO | WO 2009/014552 A1 | 1/2009 |
| WO | WO-2009014552 | 1/2009 |
| WO | WO-2011008746 | 1/2011 |

OTHER PUBLICATIONS

Zheng, et al., 'G-Protein Coupled Receptor-Associated Sorting Protein 1 (GASP-1), a Ubiquitous Tumor Marker'; Experimental and Molecular Pathology, vol. 93, No. 1, pp. 111-115, 2012.
Notification of Transmittal of the International Search Report and the Written Opinion of the International Searching Authority, or the Declaration Issued for International Application No. PCT/US2013/039430 Completed Jul. 22, 2013 and Mailed Jul. 23, 2013.
Ariazi, E A, et al, "Estrogen Receptors as Therapeutic Targets in Breast Cancer", Current Topics in Medicinal Chemistry, 6(3), 181-202 (2006).
Barton, C L, "Commercial Opportunities from Biomarkers Transforming Drug Discovery, Clinical Development and Molecular Diagnostic", Business Insights Ltd. (2006).
Baselga, J, "Targeting Tyrosine Kinases in Cancer: The Second Wave", Science, 312 (5777), 1175-1178 (2006).
Bordier, J. Biol. Chem., 256, 1604-1607 (1981).

(Continued)

*Primary Examiner* — Alana Harris Dent
(74) *Attorney, Agent, or Firm* — RatnerPrestia (57) ABSTRACT

A method for determining whether early stage cancer is present in a subject comprises detecting the expression level of GASP-1 in the subject by detecting the amount of GASP-1 peptide fragments present in a biological sample of the subject. Because cancer can be detected at an early stage, therapeutic targeting may be initiated before cancer reaches late stage (e.g., before the development of overt symptoms). A method for treating early stage cancer in a subject comprises administering to the subject an effective amount of a GASP-1 inhibitor to inhibit the progression of early stage cancer to late stage cancer. A Competitive ELISA capable of detecting GASP-1 peptide fragments at a concentration of less than 1 ng/ml was developed.

5 Claims, 6 Drawing Sheets

(56) References Cited

OTHER PUBLICATIONS

Corthals, G L, et al, "The Dynamic Range of Protein Expression: A Challenge for Proteomic Research", Electrophoresis 21, 1104-1115 (2000).
Database Geneseq [Online] XP002607582, Accession No. GSP:ADP83499 (2004).
Database Geneseq [Online] XP002607583, Accession No. GSP:ADP83500 (2004).
Database Geneseq [Online] XP002607585, Accession No. GSP:ADP83502 (2004).
Database Geneseq [Online] XP002607587, Accession No. GSP:ADV606477 (2005).
Database Geneseq [Online] XP002607581, Accession No. GSP:ADP83402 (2004).
Database Geneseq [Online] XP002607584, Accession No. GSP:ADP83400 (2004).
Database Geneseq [Online] XP002607586, Accession No. GSP:ADP83501 (2004).
Dennis, M S, et al, "Albumin Binding as a General Strategy for Improving the Pharmacokinetics of Proteins", J. Biol. Chem., 277, 35035-35043 (2002).
Druker, B J, "Imatinib as a Paradigm of Targeted Therapies", Advances in Cancer Research, 91, 1-30 (2004).
Duffy, M J, "Predictive Markers in Breast and Other Cancers: A Review", Clinical Chemistry, 51(3), 494-503 (2005).
Filardo E, et al, "Activation of the Novel Estrogen Receptor G Protein-Coupled Receptor 30 (GPR30) at the Plasma Membrane", Endocrinology, 148, 3236-3245 (2007).
Gallent, Methods Mol. Biol., 421, 53-60 (2008).
Gasparini, G, et al, "Is Tailored Therapy Feasible in Oncology?", Critical Reviews in Oncology/Hematology, 57(1), 79-101 (2006).
Ghimenti, Breast Cancer Res., 2(Suppl I), Pl.15(Excerpt) (2000).
Graff, Cancer Research, 68, 631-634 (2008).
Hayes, D F, "Prognostic and Predictive Factors Revisited", Breast, 14(6), 493-499 (2005).
He, P, "The Human Plasma Proteome: Analysis of Chinese Serum Using Shotgun Strategy", Proteomics, 5, 3442-3453 (2005).
Hosaka, Cancer Sci, 97, 623-632 (2006).
International Application Serial No. PCT/US2010/041813,International Search Report dated Nov. 2, 2011.
Kim, Breast Cancer Research,II:R22,1-12 (2009).
Kohwi-Shigematsu, The Medical News, 1-4 (2008).
Lowenthal, M S, et al, "Analysis of Albumin-Associated Peptide and Proteins From Ovarian Cancer Patients", Clinical Chemistry, 51, 1933-1945 (2005).
Lowrie, Brit. J. Cancer, 94,1663-1671 (2006).
Merrell, K, et al, "Analysis of Low-abundance, Low-molecular-weight Serum Proteins Using Mass Spectrometry", J. Biomol. Tech., 15, 238-248 (2004).
Moser, E, et al, "G Protein-coupled Receptor Associated Sorting Protein-1 Regulates the Postendocytic Sorting of Seven-transmembrane-spanning G Protein-coupled Receptors", Pharmacology, 86, 22-29 (2010).

O'Farrell, J. Biol. Chem., 250, 4007-4021 (1974).
O'Farrell, P H, "High Resolution Two-dimensional Electrophoresis of Proteins", J. Biol. Chem 250, 4007-4021 (1975).
Porter, Proc. Natl, Acad. Sci., 100, 10931-10936 (2003).
Rini, Clinical Cancer Research, 14, 1286-1290 (2008).
Ryberg, E, et al, "The Orphan Receptor GPR55 is a Novel Cannabinoid Receptor", Brit. J. Pharmacol., 152(7), 1092-1101 (2007).
Simonin, F, et al, "Identification of a Novel Family of G Protein-coupled Receptor Associated Sorting Proteins", J. Neurochem., 89, 766-775 (2004).
Sonora, J Histochem Cytochem, 54, 289-299 (2006).
Thomas, P, et al, "Binding and Activation of the Seven-transmembrane Estrogen Receptor GPR30 by Environmental Estrogens: A Potential Novel Mechanism of Endocrine Disruption", J. Steroid Biochem and Molr Biol., 102, 175-179 (2006).
Tuszynski, G P, et al, "G-protein Coupled Receptor-associated Sorting Protein 1 (GASP-1), A Potential Biomarker in Breast Cancer", Exp. Mol. Pathol., 91, 608-613 (2011).
Vonderhaar, Endocrine-Related Cancer, 6, 389-404 (1999).
Whistler, J, et al, "Modulation of Postendocytic Sorting of G Protein-coupled Receptors", Science, 297, 615-620 (2002).
Wirtenberger, Carcinogenesis, 27, 593-598 (2006).
Yeon, C H, et al, "Anti-erbB-2 Antibody Trastuzumab in the Treatment of HER2-amplified Breast Cancer", Investigational New Drugs, 23(5), 391-409 (2005).
Yonan, Anal. Biochemistry, 338, 159-161 (2005).
Devine P.L. et al., CA15-3, CASA, MSA, and TPS as Diagnostic Serum Markers in Breast Cancer, Breast Cancer Research and Treatmnet, Springer, NY, NY, vol. 34, No. 3 1995, pp. 245-251.
Price et al., High Molecular Weight Epithelial Mucins as Markers in Breast Cancer ,European Journal of Cancer and Clinical Oncology, Pergamon Press Ltd, vol. 24, No. 12, 1988, pp. 1799-1804.
Hollingsworth et al., Nature Reviews, vol. 4, 1:45-60 (2004) (Excerpt).
Database Geneseq [Online] XP002720903, Accession No. GSP:AAE11228 (2001).
Database Geneseq [Online] XP002720904, Accession No. GSP:ARL91745 (2008).
PCT/US2010/041813 International Search Report by Marco Montrone dated Nov. 2, 2011.
Partial European Search Report, Appl. No. EP 13 18 8276 dated Feb. 26, 2014.
Sjövall, et al.; *The Significance of Serum CA 125 Elevation in Malignant and Nonmalignant Diseases*; Gynecologic Oncology 85, 175-178 (2002).
M. Schuchard, et al.; *Comparison of Precipitation Methods Following Depletion of Twenty High Abundance Proteins from Human Plasma*, 3 pages, publically available Jan. 11, 2006.
Non-Final Office Action Issued for U.S. Appl. No. 13/384,014 Dated Jan. 20, 2015.

\* cited by examiner

G-PROTEIN COUPLED RECEPTOR-ASSOCIATED SORTING PROTEIN 1 AS A CANCER BIOMARKER

CROSS REFERENCE TO RELATED APPLICATIONS

This application is a continuation-in-part of U.S. application Ser. No. 13/464,174, filed May 4, 2012, which is a continuation-in-part of U.S. application Ser. No. 13/384,014, filed Jan. 13, 2012, which is a national phase application of PCT International Application PCT/US2010/041813, filed Jul. 13, 2010, claiming priority to U.S. Provisional Application No. 61/225,254, filed Jul. 14, 2009, the contents of which applications are incorporated by reference herein, in their entireties and for all purposes.

FIELD OF THE INVENTION

This invention relates to the use of G-protein coupled receptor-associated sorting protein 1 (GASP-1), peptide fragments thereof, and GASP-1 nucleic acids as early or late stage cancer biomarkers, and the use of such biomarkers to determine a diagnosis, prognosis, or therapeutic treatment for a subject.

BACKGROUND OF THE INVENTION

Over the next decade biomarkers are predicted to significantly change the efficiency and economics of drug discovery and development. The pharmaceutical industry is shifting its focus from biomarkers that simply differentiate therapeutic responder/non-responder populations to identifying new biomarkers that are themselves validated as therapeutic targets. It is estimated that if biomarker data could improve just 10% of the critical decisions in the drug development process, then savings of up to $100 million per drug could be achieved (Barton, 2006). The global biomarker market is estimated to reach $20.5 billion by 2014, growing at a CAGR of about 20% from 2009 to 2014. Market growth has been primarily driven by high demand for biomarkers for drug discovery and development.

Presently, oncology is the most active field for disease biomarker research and development, primarily because cancer therapy routinely provides biopsy and surgically excised tissues that are utilized in new therapy development. For example, imatinib targets an enzyme produced as a result of chromosomal translocation discovered to be associated with chronic myelogenous leukemia (Druker, 2004; Baselga, 2006). In breast cancer, the expression of the estrogen receptor is used as a biomarker for prognosis and to identify women who are likely to benefit from antiestrogen therapy (Duffy, 2005; Ariazi et al., 2006), while over-expression of HER2 (a growth factor receptor) serves as a biomarker for prognosis and for treatment with trastuzumab (Yeon and Pegram, 2005; Duffy, 2005; Baselga, 2006). However, despite these notable achievements, relatively few patients ever benefit from biomarker-guided therapy since most biomarkers are identified in only a few percent of the population, and very few are sufficiently validated as drug targets. Most candidate biomarkers never advance beyond the discovery phase, and the number of biomarkers validated for use in drug development or qualified for clinical applications is still very small (Duffy, 2005; Hayes, 2005; Gasparini et al., 2006). There is a critical need to identify more biomarkers, especially early stage cancer biomarkers, as therapeutic targets and to develop drugs that can benefit the rest of the cancer patients.

Biomarker research exploded primarily due to the use of proteomics approaches focusing on identifying differences in protein structure and abundance between diseased and normal states. Once identified, these biomarker proteins can be utilized for developing diagnostic tools, and because they are functional molecules, they are also more likely to be valid therapeutic targets.

The accessibility and presence of a large number of proteins in blood plasma make it an excellent matrix in which to search for new biomarkers. However, the estimated dynamic range of various protein concentrations in human serum is up to 10 orders of magnitude (Corthals et al, 2000), making the rapid identification of individual disease-associated proteins a tremendous analytical challenge. While total serum protein concentration is approximately 70-90 mg/ml, most useful biomarkers, such as cytokines and prostate specific antigen, are present in the picogram range, and disease-specific changes can be expected to be incrementally small, especially in the early stages of disease (Merrell et al., 2004). Compounding these problems, many disease-specific proteins (e.g. cancer biomarkers) are degraded inside the cell by proteolytic enzymes, generating peptide fragments that are subsequently released into the blood. Being low molecular weight in nature, these peptide fragments generally have a half-life of only about two hours and most of them are cleared from circulation by the kidney (Lowenthal et al, 2005).

In order to overcome challenges presented by low concentration and rapid turnover of potentially useful peptides, the albumin-associated fraction of proteins and peptides have been investigated as a source of useful new disease-specific biomarkers. Albumin, the most abundant plasma protein (40-50 mg/ml), functions as a scaffold for binding small molecules, lipids, and proteins in the extracellular space. It has been found to form complexes with peptide hormones such as insulin and glucagons; bradykinin, serum amyloid A, interferons, the amino-terminal peptide of HIV-1, gp41, and the 14-kDa fragment of streptococcal protein G, among others. Interestingly, it was found that a small percentage of the secreted peptide fragments from degraded cancer proteins have high affinity for serum albumin complexes which increase their half-life to about 19 days (Lowenthal et al, 2005). By their association with serum albumin to form complexes, the longevity of these cancer-related peptide fragments (cancer peptide motifs) can be increased by approximately 60 to 100-fold (Dennis et al, 2002). Due to its high affinity for such a diverse range of ligands, the serum albumin population is expected to be highly heterogeneous, most likely comprising hundreds of different albumin complexes.

Techniques currently in use were designed to separate proteins or peptides and they cannot be used to separate serum albumin complexes. For example, current technologies for protein and peptide separation include electrophoresis (one-dimensional and two-dimensional; capillary, etc.), chromatography (reversed-phase, ion exchange, size exclusion, affinity, etc), and solvent precipitation. Different combinations of these multidimensional separation technologies have been used to separate a mixture of proteins. For example, a sample is separated into individual spots or fractions using different separation techniques, and the individual proteins are then analyzed by mass spectrometry to establish their identity. A "shotgun" strategy was also developed where, without prior separation, entire samples containing a mixture of a large number of different proteins, such as plasma or serum, are proteolytically digested into peptides by trypsin (He, et al, 2005). The peptides in the tryptic digest are then separated by multidimensional separation techniques and then analyzed by mass spectrometry to establish the identities of the proteins present in the sample. It was hoped that these multidimensional separation technologies would offer significant enhancement in sensitivity for low abundance proteins by removing the masking effect of the highly abundant proteins, thereby enabling deeper penetration into the plasma proteomes. However, since none of these technologies separate serum albumin complexes, they have not yielded useful biomarkers.

Even the most widely used technology for protein separation, 2-dimensional polyacrylamide gel electrophoresis (2-D PAGE), introduced by O'Farrell (1975), cannot separate serum albumin complexes, as it is typically conducted under "denaturing" conditions. Additionally, 2-D PAGE has many other shortcomings including requiring large amounts of samples (about 50 to 100 μg of protein per experiment) and producing a rather streaky and mostly diffused profile when serum is analyzed. Furthermore, proteins separated by 2-D PAGE are required to be "blotted" or transferred onto blotting membranes such as polyvinylidene difluoride (PVDF) for Western blot analysis. The efficiency of protein blotting is also variable.

As described in WO 2011/008746, the present inventors developed a new electrophoresis procedure that separates protein complexes directly on the PVDF membrane, thus bypassing both the cumbersome, time-consuming gel electrophoresis and its subsequent blotting steps (Chang and Yonan, 2008; Chang et al., 2009). The separation of albumin complexes in the present inventors' 2-D High Performance Liquid Electrophoresis (2-D HPLE) is based on their net charge or isoelectric points (pI). The association of a newly produced cancer peptide fragment (cancer peptide motif) with a pre-existing albumin complex changes its pI and this new complex migrates to a different location on the PVDF membrane, allowing its detection among hundreds of already present albumin complexes. Because it focuses on disease-specific protein fragments, the technique enables not only the identification of new cancer protein biomarkers, but also identifies the cancer peptide motifs within these proteins. When LC/MS/MS analysis is preceded by fraction separation using 2-D HPLE, its dynamic range is enhanced to the $10^{10}$ range required for detecting low copy number cancer biomarkers, a sensitivity that has not previously been achieved using other protein separation techniques.

Using a yeast two-hybrid screen with the carboxyl-terminal tail of a G protein-coupled receptor (delta opioid receptor) as bait, Whistler et al., (2002) discovered that one of its interacting partners is G-protein coupled receptor-associated sorting protein 1 (GASP-1). GASP-1 was later found to interact with cytoplasmic tails of many other G-protein coupled receptors including D2 dopamine receptor/DRD2, beta-2 adrenergic receptor/ADRB2 and D4 dopamine receptor/DRD4 (Simonin et al., 2004). GASP-1 is involved in silencing signals by targeting receptors for degradation in lysosomes and functional down-regulation of a variety of G-protein coupled receptors (GPCRs).

In the same study by Whistler et al (2002), important structure-function experiments were performed and identified the C-terminal fragment of GASP-1 (cGASP-1) as the domain of the protein that binds to lysosomes. Interestingly, these truncated forms of GASP-1 (cGASP-1) were also shown to function as dominant negative mutants inhibiting degradation and favoring the recycling of delta opioid receptor. These experiments provided the first evidence that GASP-1 had the capacity to regulate either the recycling or degradation of GPCRs. Since then, the trafficking of numerous GPCRs has been shown to be regulated by GASP-1 (Moser et al., 2010).

As described in WO 2011/008746, the present inventors have used 2-D HPLE to investigate disease-specific albumin complexes in plasma from patients with breast cancer (Chang, et al, 2009; Tuszynski et al., 2011). One of the newly identified serum albumin complexes from Stage I breast cancer was cut out from the PVDF membrane after 2-D HPLE and subjected to on-membrane digestion with trypsin. The cancer peptide motif was identified as a 16 amino acid sequence of EEASPEAVAGVGFESK (SEQ ID NO: 1) by liquid chromatography with tandem spectrometry sequencing of individual peptides (LC/MS/MS). Protein identity was determined from database searches of virtual tryptic peptide databases and fragmentation spectra of tryptic peptides. This 16-amino acid sequence came specifically from GASP-1. No studies had previously linked GASP-1 to cancer pathogenesis. However, the present inventors used polyclonal antibody raised against the 16-amino acid sequence from GASP-1 to detect the expression of GASP-1 and its fragments in tumor extracts of cancer patients (Chang et al., 2009). It was found that GASP-1 was expressed in all 7 cases of late stage (Stage II and Stage III) breast cancer patients but not in adjacent normal tissue as revealed by Western Blot analysis (Chang, et al., 2009; Tuszynski et al., 2011). Thus, the 2-D HPLE process not only discovered the 1,395 amino acid GASP-1 as a new late stage cancer protein biomarker but also identified specifically the 16-amino acid residue cancer peptide motif (covering amino acid residues 850 to 865) in this protein.

Currently, no reports on biomarkers for the detection of early stage cancer are available. People are regularly told to watch for early symptoms of cancer. However, by the time symptoms occur, many tumors have already grown quite large and may have metastasized. Moreover, many cancers have no symptoms. There remains a need for biomarkers of early stage cancer to enable the detection, diagnosis, and treatment of cancer at its earliest stages of development.

SUMMARY OF THE INVENTION

According to various aspects of the invention, expression levels of GASP-1, peptide fragments thereof, GASP-1 mRNA, or GASP-1 cDNA, either alone or as part of a microarray or PCR array, may be used as a diagnostic tool or biomarker that provides early stage information on the presence, progression, and metastatic potential of many cancers. An embodiment of the present invention provides a method for determining whether early or late stage cancer is present in a subject comprising detecting the expression level of GASP-1 in the subject. An exemplary embodiment of the present invention provides a method for determining whether early stage cancer is present in a subject comprising detecting the expression level of GASP-1 in the subject. Detecting the expression level of GASP-1 in a subject may comprise detecting an amount of GASP-1 peptide fragments, such as EEASPEAVAGVGFESK (SEQ ID NO: 1), present in a biological sample of the subject.

A further aspect of the invention relates to the therapeutic targeting of GASP-1, peptide fragments thereof, GASP-1 iRNA (inhibitory RNA), GASP-1 shRNA (short hairpin RNA), GASP-1 mRNA, GASP-1 cDNA, or interacting partners of GASP-1 for the purpose of inhibiting the progression (e.g., spread) of cancer. Because methods of the present invention can detect early stage cancer, therapeutic targeting may be initiated before cancer reaches late stage (e.g., before the development of overt symptoms). An embodiment of the present invention provides a method for treating early stage cancer in a subject comprising administering to the subject an effective amount of a GASP-1 inhibitor to inhibit the progression of early stage cancer to late stage cancer.

The present invention further provides a modified ELISA (enzyme-linked immunosorbent assay), referred to as a "Competitive ELISA," for detecting GASP-1 and fragments thereof in biological samples. The "Competitive ELISA" is capable of detecting GASP-1 peptide fragments of the present invention at a concentration of less than 1 ng/mL.

DETAILED DESCRIPTION OF THE INVENTION

Biomarkers that appear during early stage cancer can be used for both detection and screening of diseases before the appearance of symptoms. Because many cancers do not show symptoms, particularly during early stages, biomarkers that are over-expressed at an early stage and then increase in level during disease progression can provide clinicians with important information that will result in earlier detection, more successful treatment, faster patient cure, and reduced costs.

As described in WO 2011/008746, Western blot analysis was used to show that G-protein coupled receptor-associated sorting protein 1 (GASP-1) was highly expressed in each of the seven late stage (Stage II and Stage III) breast cancer patients. GASP-1 was only expressed in the tumor cells (T) but not in the adjacent normal (i.e., non-cancerous) cells (C) from the same patients. Fragments of GASP-1 were originally discovered from analysis of serum albumin complexes from Stage 1 breast cancer patients using 2-D HPLE technology. These results suggested that either GASP-1 (expressed in Stage 1) is stable and persists into Stage II and Stage III breast cancer, or GASP-1 is continuously expressed throughout Stages I, II, and III.

Because they are easily obtained, practically all reported studies in the literature are conducted using late stage breast cancer samples (e.g., Stages I to IV) with regard to breast cancer progression. Importantly, although cancer can develop in virtually any of the body's tissues, and each type of cancer has its unique features, the basic processes that produce cancer may be quite similar in all forms of the disease. In this regard, the present inventors have now unexpectedly discovered that over-expression of GASP-1 occurs at very early stage cancer, probably at the beginning of the disease process involving the transforming of a normal cell to a cancerous cell. This surprising finding has far-reaching implications because, up to now, no biomarkers for early detection of any cancer (e.g., prior to late stage cancer) have been discovered. Many cancers have no symptoms and by the time symptoms occur many tumors already have grown quite large and may have metastasized. The present discovery of early biomarkers for many cancers allows the detection and diagnosis of cancer to be pushed back to its earliest stages of development. Medical intervention for cancer may now become focused at identifying incipient disease and preventing its progression to overt disease, rather than treating the cancer after it is well-established.

The present inventors have not only discovered that GASP-1 is over-expressed at the very early stage of many cancers, but that its expression level increases during the progression of cancers. GASP-1 regulates the availability of many G protein coupled receptors (on the plasma membrane) required for continuous cancer cell growth. Furthermore, in many cancers, peptide fragments derived from the over-expressed GASP-1 are released into the bloodstream and the increase in the levels of the peptide fragments is indicative of the presence and severity of cancer. Because of their appearance at early stages of cancer, both the GASP-1 protein and peptide fragments thereof can be used as early stage biomarkers for detection and screening of cancers before symptoms appear. No biomarker studies involving detection of early stage cancer have been reported. The present invention deals with biomarkers that appear in precancerous (benign) and other early stages (such as dysplasia) before tumors are found.

Thus, one embodiment of the invention employs peptide fragments derived from GASP-1 as biomarkers specific for early stage cancer. The cancer peptide fragments are detected because GASP-1 is degraded by proteolytic enzymes (inside the cancer cell) generating fragments which are subsequently secreted into the bloodstream. Most of these peptide fragments are removed by the kidney and disappear from circulation quickly. Only a very small fraction of the peptide fragments (those containing cancer peptide motifs) has high binding affinity for pre-existing serum albumin complex generating new (cancer) serum albumin complex. As described in WO 2011/008746, the newly-formed cancer complex (out of several hundred serum albumin complexes already present in the circulation) can be separated by a 2-D High Performance Liquid Electrophoresis (2-D HPLE) employing polyvinylidine difluoride (PVDF) as the supporting matrix (Chang et al. 2009). The amino acid sequence of the cancer peptide motif from the isolated cancer serum albumin complex is then identified by mass spectrometry (LC/MS/MS).

The cancer peptide motif may have the same length as the cancer peptide fragment sequestered in the serum albumin complex. Most likely the cancer peptide motif will have a shorter length than the original cancer peptide fragment. This is because the cancer peptide motif (peptide fragment identified by LC/MS/MS) is recovered only after the digestion of the sequestered cancer peptide fragment with an enzyme, such as trypsin, which results in removing some amino acid residues at the carboxyl terminal end of the cancer peptide fragment. The removed amino acid residues are not recovered in mass spectrometric analysis and therefore lost. Similarly, some of the amino acids of the cancer peptide fragment at the N-terminal end may also be removed by the enzymatic digestion and not recovered. It is therefore to be expected that the cancer peptide motif will have a shorter amino acid sequence when compared to the cancer peptide fragment where it originates. A cancer peptide motif having an amino acid sequence of EEASPEAVAGVGFESK (SEQ ID NO: 1) was recovered from GASP-1 (Chang et al. 2009). In general, a cancer peptide motif represents only about 1% to 3% of a cancer protein (Chang et al. 2009). For example, EEASPEAVAGVGFESK (SEQ ID NO: 1) has 16 amino acids (residues 850 to 865) of the 1,395 amino acid G-protein coupled receptor-associated sorting protein 1 (GASP-1). This particular peptide sequence is unique for cancer detection because no other human proteins contain this sequence.

As used herein, "early stage cancer" includes any pre-cancerous state prior to late stage cancer, including but not limited to benign conditions, conditions prior to invasive carcinoma, and/or conditions prior to the development of a cancerous tumor. With regard to breast cancer, "early stage cancer" includes any pre-cancerous state prior to stage I, stage II, stage III, or stage IV cancer, as described in more detail below. Examples of early stage breast cancer include benign conditions (e.g., non-proliferative lesions, proliferative lesions without atypia, and proliferative lesions with atypia), dysplasia, and/or carcinoma in situ. With regard to cancers other than breast cancer (e.g., glioma, bladder cancer, colon cancer, esophagus cancer, hepatocellular carcinoma, larynx cancer, lung cancer, skin cancer, ovarian cancer, prostate cancer, pancreatic cancer, renal cancer, or stomach cancer), "early stage cancer" includes any pre-cancerous state prior to late stage cancer, such as those that correspond to stage I, stage II, stage III, or stage IV in breast cancer.

Benign conditions include any non-cancerous abnormality that has the potential to develop into late stage cancer. As used herein, "cancer-free" refers to a subject who is free of either early stage or late stage cancer, or to tissue of a subject that is free of either early stage or late stage cancer. A subject as used herein is preferably an animal, including but not limited to mammals, and most preferably human.

An embodiment of the present invention provides a method for determining whether early or late stage cancer is present in a subject comprising detecting the expression level of GASP-1 in the subject. An exemplary embodiment of the present invention provides a method for determining whether early stage cancer is present in a subject comprising detecting the expression level of GASP-1 in the subject. The method is preferably performed on a subject that has not developed late stage cancer (e.g., stage I, II, III, or IV cancer) or overt symptoms of cancer, such as a cancerous tumor. For example, the subject has not been diagnosed with late stage cancer, such as an invasive carcinoma. The subject may have one or more benign conditions, one or more conditions prior to invasive carcinoma, and/or one or more conditions prior to the development of a cancerous tumor (e.g., the subject may have a non-cancerous abnormality, such as a benign lesion). Thus, methods of the present invention can detect early stage cancer by using GASP-1, GASP-1 peptide fragments, or GASP-1 nucleic acids as early stage biomarkers.

The expression level of GASP-1 in the subject can be compared to the expression level of GASP-1 in a cancer-free subject (or the expression level of GASP-1 in a biological sample that is cancer-free) to determine whether GASP-1 is over-expressed in the subject. A higher expression level of GASP-1 in the subject compared to the expression level of GASP-1 in the cancer-free subject (or in the cancer-free biological sample) indicates the presence of cancer in the subject. In a subject that does not have late stage cancer (e.g., a subject that does not have stage I, II, III, or IV breast cancer), a higher expression level of GASP-1 in the subject compared to the expression level of GASP-1 in the cancer-free subject (or in the cancer-free biological sample) indicates the presence of early stage cancer in the subject. In alternative embodiments, the expression level of GASP-1 in the subject can be compared to predetermined reference data which correlate expression levels of GASP-1 with various stages of cancer (e.g., cancer-free, early stage cancer, and/or late stage cancer) to determine whether GASP-1 is over-expressed in the subject.

According to preferred embodiments, detecting the expression level of GASP-1 in a subject comprises detecting an amount of GASP-1 peptide fragments present in a biological sample of the subject. The peptide fragments preferably have at least about 6, at least about 10, at least about 15, at least about 20, at least about 25 or at least about 30 amino acids. The GASP-1 peptide fragments may comprise, for example, between about 6 to about 50 amino acids, between about 10 to about 30 amino acids, or between about 15 to about 20 amino acids. The GASP-1 peptide fragments may comprise or consist of the sequence EEASPEAVAGVGFESK (SEQ ID NO: 1). Alternatively, the GASP-1 peptide fragments comprise or consist of fragments of the sequence EEASPEAVAGVGFESK (SEQ ID NO: 1).

Non-limiting examples of biological samples discussed herein include blood, urine, spinal fluid, amniotic fluid, serum, gingival, cervicular fluid, lachrymal fluid, lymph, mammary gland secretions, mucus, saliva, semen, tears, vaginal secretions, and vitreous humor. Biological samples may be obtained from any type of biological material, including tissues, cells, fluids, and the like from a subject. In alternative embodiments, the biological sample comprises serum or tissue that is potentially pre-cancerous (such as tissue that comprises a benign lesion, e.g., a proliferative lesion, a non-proliferative lesion, or tissue exhibiting dysplasia) obtained from the subject. For example, the method may comprise obtaining a biological sample from a subject that does not have late stage cancer (e.g., from potentially pre-cancerous tissue in the subject), detecting an amount of GASP-1 peptide fragments present in the biological sample, and comparing the amount of GASP-1 peptide fragments present in the biological sample to an amount of GASP-1 peptide fragments present in a cancer-free tissue, or to predetermined reference data. In particular embodiments, the potentially pre-cancerous tissue and the cancer-free tissue may be obtained from the same subject.

According to particular embodiments, detecting the amount of GASP-1 peptide fragments present in a biological sample of the subject comprises contacting the biological sample with a binding agent that selectively binds GASP-1 peptide fragments and detecting the amount of GASP-1 peptide fragments that bind to the binding agent. The binding agent is preferably an antibody. The antibody may be selected, for example, from a polyclonal antibody, a monoclonal antibody, a single chain antibody, a Fab, and an epitope-binding fragment of an antibody. The binding agent may be bound to a radioactive label, a fluorescent label, a chemiluminescent label, or a bioluminescent label. Methods for detecting the amount of GASP-1 peptide fragments present in a biological sample of the subject may comprise using an immunoassay (e.g., an ELISA) that is well-known in the art. As discussed in more detail below, a "Competitive ELISA" (enzyme-linked immunosorbent assay) of the present invention is preferably used to detect the amount of GASP-1 peptide fragments in the subject.

Embodiments of the present invention further include treating early stage cancer in a subject by administering to the subject an effective amount of a GASP-1 inhibitor or antagonist to inhibit the progression of early stage cancer to late stage cancer (e.g., to slow down or arrest the progression of early stage cancer to late stage cancer). In a preferred embodiment, a GASP-1 inhibitor is administered to a subject that has early stage cancer. For example, the GASP-1 inhibitor may comprise a biomolecule (e.g., an antibody) selective for GASP-1 or a peptide fragment thereof (e.g., an antibody selective for a peptide fragment of SEQ ID NO: 1), or a small inhibitory RNA (siRNA) or short hairpin RNA (shRNA) selective for a GASP-1 cDNA sequence or SEQ ID NO: 1. Alternatively, the GASP-1 inhibitor is selective for an interacting partner of GASP-1 or its peptide fragments. Because methods of the present invention can detect early stage cancer, therapeutic targeting is preferably initiated before cancer becomes late stage (e.g., prior to stage I in breast cancer). As used herein, the term "effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent progression of early stage cancer to late stage cancer.

A GASP-1 inhibitor or antagonist may be administered in a pharmaceutically acceptable carrier. As used herein, the term "pharmaceutically acceptable carrier" refers to a diluent, adjuvant, excipient, or vehicle with which a GASP-1 inhibitor or antagonist is administered. Such carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when a compound is administered intravenously. Saline solutions and aqueous dextrose and glycerol solutions can also be employed as liquid carriers, particularly for injectable solutions. Suitable excipients include starch, glucose, lactose, sucrose, gelatin, silica gel, sodium stearate, glycerol monostearate, talc, sodium chloride, glycerol, propylene glycol, water, ethanol and the like. A pharmaceutically acceptable carrier can also include minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be included in a carrier. Methods for producing compounds in combination with carriers are known to those of skill in the art.

Non-limiting examples of the types of early stage cancers that methods of the present invention may be used to detect and/or treat include early stage breast cancer (including early stage triple-negative breast cancer), early stage bladder cancer, early stage colon cancer, early stage esophagus cancer, early stage hepatocellular carcinoma, early stage larynx cancer, early stage lung cancer, early stage skin cancer, early stage ovarian cancer, early stage prostate cancer, early stage pancreatic cancer, early stage renal cancer, and early stage stomach cancer.

Another embodiment of the present invention provides a method for producing antibodies, comprising administering an effective amount of a peptide fragment of the present invention (from the over-expressed GASP-1 protein) to an immunologically competent host, and recovering antibodies from the host that are specific for the peptide fragment. Antibodies against peptide fragments from GASP-1 are highly specific "peptide antibodies" recognizing only a small region of the cancer protein (rather than the entire protein). Because the antibodies are raised against a very small region (or unique region) and not to the whole protein, they will be highly specific and will generally not be able to cross-react with other protein in the body. Antibodies directed against an entire cancer protein as commonly used commercially will likely miss a specific cancer peptide motif and therefore render them ineffective (or much less effective) in detecting a particular cancer peptide fragment. Furthermore, therapeutic drugs targeting a short cancer peptide (or cancer peptide motif) sequence will be highly specific and will be expected to have much fewer side effects, if any. Therapeutics of the present invention include biomolecules that have high affinity for the GASP-1 peptide fragments of the present invention. Therapeutics can also target the interacting partners of GASP-1.

In one aspect of the invention, an antibody that binds specifically to a cancer peptide fragment (or a cancer peptide motif) from GASP-1 protein may be obtained. For example, a rabbit antibody has been generated to bind specifically to a cancer peptide motif having an amino acid sequence EEASPEAVAGVGFESK (SEQ ID NO: 1). The antibody may be used to detect the cancer peptide fragment, or cancer peptide motif, or its corresponding GASP-1 protein in a biological sample from a subject. Alternatively, the over-expressed GASP-1 protein in cancers can be detected by using antibodies against other regions of this protein.

An antibody of the present invention may also be used to inhibit the growth of a cancer cell and/or the progression from early stage cancer to late stage cancer. The antibody may specifically bind a GASP-1 peptide fragment of the present invention, such as a cancer peptide motif having an amino acid sequence EEASPEAVAGVGFESK (SEQ ID NO: 1). The antibody may also be used to treat a cancer patient by administering an effective amount of the antibody to the subject, whereby the antibody inhibits tumor growth or cancer migration in the subject. Suitable tumors or cancers for early stage antibody treatment include breast cancer, triple-negative breast cancer, glioma, bladder cancers, colon cancer, esophagus cancer, hepatocellular carcinoma, larynx cancer, lung cancer, skin cancer, ovarian cancer, prostate cancer, pancreatic cancer, renal cancer, and stomach cancer. The antibody treatment may be used alone or in conjunction with other treatments.

A small inhibitory RNA (siRNA) or a small hairpin RNA (shRNA) complementary to the reading frame of GASP-1 cDNA or the 3 prime or 5 prime untranslated sequence of GASP-1 cDNA may be used to inhibit or arrest the growth of a cancer cell and/or the progression from early stage cancer to late stage cancer. The siRNA or shRNA may specifically bind a GASP-1 mRNA coding for a peptide fragment of the present invention, such as a cancer peptide motif having an amino acid sequence EEASPEAVAGVGFESK (SEQ ID NO: 1). The siRNA or shRNA may also be used to treat a cancer patient by administering an effective amount of the RNA to the subject either directly by injecting the oligonucleotide, or by generating the oliogonucliotide using an appropriate DNA vector such as adenovector, whereby the RNA inhibits tumor growth or cancer migration in the subject. Suitable tumors or cancers for early stage antibody treatment include breast cancer, triple-negative breast cancer, glioma, bladder cancers, colon cancer, esophagus cancer, hepatocellular carcinoma, larynx cancer, lung cancer, skin cancer, ovarian cancer, prostate cancer, pancreatic cancer, renal cancer, and stomach cancer. The treatment may be used alone or in conjunction with other treatments A disease may be caused by DNA damage (e.g., mutation) in genes that regulate cell growth and division. Cancer may cause the body to produce abnormal proteins, over-production or under-production of protein. According to embodiments of the present invention, over-expression of cancer protein in the present invention may be detected either from levels of GASP-1 protein, peptide fragments thereof, or its nucleic acid. For example, GASP-1 or its peptide fragments may be detected in tissues, cells, cell membrane, cytoplasm, cell extract, or biological fluid (such as blood, serum, urine). GASP-1 nucleic acids may be detected from mRNA encoding GASP-1, either directly or indirectly (e.g. via cDNA derived therefrom). According to particular embodiments, the amount of GASP-1 cDNA in a sample may be determined by microarray or PCR array.

As discussed above, in various aspects of the invention, the expression levels of GASP-1 and peptide fragments thereof may be used as a diagnostic tool or biomarker that relates to the detection and progression of breast cancer and many other cancers. A further aspect of the invention relates to the therapeutic targeting of the GASP-1 and fragments thereof for the purposes of inhibiting progression and spread of cancer. Thus, in one aspect the invention provides a method for detecting early stage cancer in a biological sample from an individual comprising assessing the level of expression of GASP-1 or peptide fragments thereof.

Benign breast disease is an important risk factor for breast cancer. Currently, no biomarkers for either benign (precancerous) or early stage breast cancer are available. The stages of breast cancer are well-defined and the process usually takes many years to progress. Breast cancer is a model system because its progression steps also occur in many other malignant cancers of epithelial tissues (carcinomas). Examples of the carcinomas are lung, prostate, colon, pancreatic cancers, etc.

The very first steps leading to breast cancer are the so-called benign conditions which cover broadly any non-cancerous breast abnormality. Some types of benign breast conditions are linked to higher breast cancer risk, while others are not. Benign conditions are further divided into three general groups, based on whether the cells are multiplying (proliferative) and whether there are abnormal cells (atypia).

In non-proliferative benign lesions, the conditions are not linked with the overgrowth of breast tissue. They do not seem to affect breast cancer risk, or if they do, the effect is very small. Proliferative lesions without atypia (hyperplasia) slightly increase cancer risk because these conditions are linked with the growth of cells in the ducts or lobules of the breast tissue. Proliferative lesions with atypia (atypical hyperplasia), on the other hand, raise the risk of cancer because these conditions are linked with the excessive growth of cells in the ducts or lobules of the breast tissue, and the cells no longer look normal. They can raise breast cancer risk about 4 to 5 times higher than normal.

Advancement of benign breast conditions to a cancerous state follows additional steps of dysplasia, carcinoma in situ, and invasive carcinoma. Dysplasia is the earliest form of pre-cancerous lesion which pathologists can recognize in a pap smear or in a biopsy. Dysplasia can be low grade or high grade which is carcinoma in situ.

In carcinoma in situ (meaning "cancer in place"), epithelial cells have lost their tissue identity and have reverted back to a primitive cell form that grows rapidly and with abnormal regulation for the tissue type. However, this form of cancer remains localized, and has not invaded past the basement membrane into tissues below the surface.

Once tumors are formed, further development of breast cancer to more advanced stages can be classified as a range of stages from Stage I to Stage IV (also referred to as late stage cancer) based on tumor size and the extent to which it has spread. Table 1 summarizes the stages.

TABLE 1

| Stage | Tumor Size | Lymph Node Involvement | Metastasis (spread) |
|---|---|---|---|
| I | Less than 2 cm | No | No |
| II | Between 2-5 cm | No or in same side of breast | No |
| III | More than 5 cm | Yes, on same side of breast | No |
| IV | Not applicable | Not applicable | Yes |

In Stage I, the primary (original) cancer is 2 cm or less in diameter and has not spread to the lymph nodes. In Stage IIA, the primary tumor is between 2 and 5 cm in diameter and has not spread to the lymph nodes. In Stage IIB, the primary tumor is between 2 and 5 cm in diameter and has spread to the axillary (underarm) lymph nodes; or the primary tumor is over 5 cm and has not spread to the lymph nodes. In Stage IIIA, the primary breast cancer of any kind that has spread to the axillary (underarm) lymph nodes and to axillary tissues. In Stage IIIB, the primary breast cancer is any size, has attached itself to the chest wall, and has spread to the pectoral (chest) lymph nodes. Finally, in Stage IV, the primary cancer has spread out of the breast to other parts of the body (such as bone, lung, liver, brain). The treatment of Stage IV breast cancer focuses on extending survival time and relieving symptoms.

The present inventors have shown that in normal breast cells, GASP-1 is either not expressed or is only very minimally expressed. A surprisingly 4 to 6-fold over-expression of GASP-1 levels has occurred even in the benign (precancerous) stage when compared to normal adjacent tissues from the same patients. GASP-1 over-expression further increases and reaches about 8-fold over-expression when the benign (precancerous) conditions are progressed to the first detectable pre-cancerous stage by pathologists (dysplasia). Further increase in expression of GASP-1 levels is observed when breast cancer progresses to more advanced late stage carcinomas (e.g. Stages I to IV).

In breast cancer about 15-20% patients test negative for estrogen, progesterone receptors, and HER2 in the lab and are called "triple-negatives." Since hormones are not supporting its growth, the cancer is unlikely to respond to hormonal therapies, including tamoxifen, Arimidex® (chemical name: anastrozole), Aromasin® (chemical name: exemestane), Fernara® (chemical name: letrozole), and Faslodex® (chemical name: fulvestrant). Triple-negative breast cancer also is unlikely to respond to medications that target HER2, such as Herceptin® (chemical name: trastuzumab) or Tykerb® (chemical name: lapatinib). In addition, triple-negative breast cancer tends to be more aggressive than other types of breast cancer. Studies have shown that triple-negative breast cancer is more likely to spread beyond the breast and more likely to recur (come back) after treatment. No biomarkers for triple-negatives are currently available. The present inventors have discovered that GASP-1 is a useful biomarker for detection and potential treatment of triple-negative breast cancer.

As described in WO 2011/008746, immunohistochemical staining was used to show that GASP-1 was highly expressed in invasive ductal carcinoma which is a very late stage breast cancer (Chang et al. 2009). The over-expression of GASP-1 was also found in late stages of many other cancers including brain, bladder, liver, lung and other tumor tissues. It was not known from these results at what stage the over-expression of GASP-1 occurs and it was not expected that the over-expression occurred during early stage cancer. The present inventors have now surprisingly found that GASP-1 over-expression starts at very early stage cancers.

Until now, different cancers have always been considered as separate diseases. The prevailing thinking is that there must be specific marker(s) for different cancers such as breast cancer, liver cancer, lung cancer, etc. The present invention dispels this notion, particularly at the early stage of cancers, as many (if not all) cancers appear to have the same original events. One of these biochemical events is the over-expression of GASP-1. GASP-1 is critically important in cancer development because it is involved in recycling many G protein receptors that are required for continuous (uncontrolled) cell growth. G protein receptors recognize signaling molecules such as growth factors, cytokines, estrogen, etc., which tell the cells to grow continuously. Cancer cells require more GASP-1 because they need more receptors on their cell surfaces. Thus, GASP-1 controls the number of receptors available for the cancer cell. As cancer progresses more GASP-1 molecules are required. In a way, GASP-1 can be considered as a "master regulator" of signal transduction processes. By establishing the requirement for GASP-1 in early cancer development, the present inventors have shown for the first time that cancer development can be caused by over-expression of a protein that regulates the availability of G protein-coupled receptors.

By establishing that GASP-1 is a general marker for very early cancer, the present invention provides methods not only the detection but also treatment of many cancers at their earliest stages of development.

According to particular embodiments, the assessment may be an immunoassay based test. For instance, ELISA or even labeled antibodies may be used in an immunoassay to evaluate levels of GASP-1 or peptide fragments thereof. Other methods well known in the art may include the use of fluorescence microscopy, Western blot analysis, mRNA Northern and slot blot analyses, enzymatic amplification and analysis of mRNA, fluorescence activated cell sorting, and so on. Methods of assessing expression of GASP-1 may be conventional in the art, for example as described in Ryberg (2007), or as set out in the Examples below.

The invention provides a new ELISA (called a "Competitive ELISA") method for detecting peptide fragments (originating from GASP-1) that are secreted into the blood or other biological fluids. As indicated earlier, over-expression of GASP-1 in cancer tissues leads to the secretion and accumulation of GASP-1 peptide fragments, including a specific fragment containing 16-amino acid sequence (EEASPEAV-AGVGFESK (SEQ ID NO: 1)), into the blood. The 16-amino acid GASP-1 fragment constitutes only about 1% of the entire protein and its amino acid sequence is unique because no other human proteins contain this particular sequence. It is highly desirable to detect this or other peptide fragments from the over-expressed GASP-1 protein.

Sandwich-type ELISA diagnostic kits have been commonly used to detect larger disease protein biomarkers but not short peptides like the ones discovered by the present inventors. In this type of analysis, two antibodies against two different regions of a protein are required. The first antibody (capture antibody) on a support with high affinity for one region of the protein captures the protein and the second antibody (detection antibody) recognizes a different epitope of the same protein.

Figure 1:
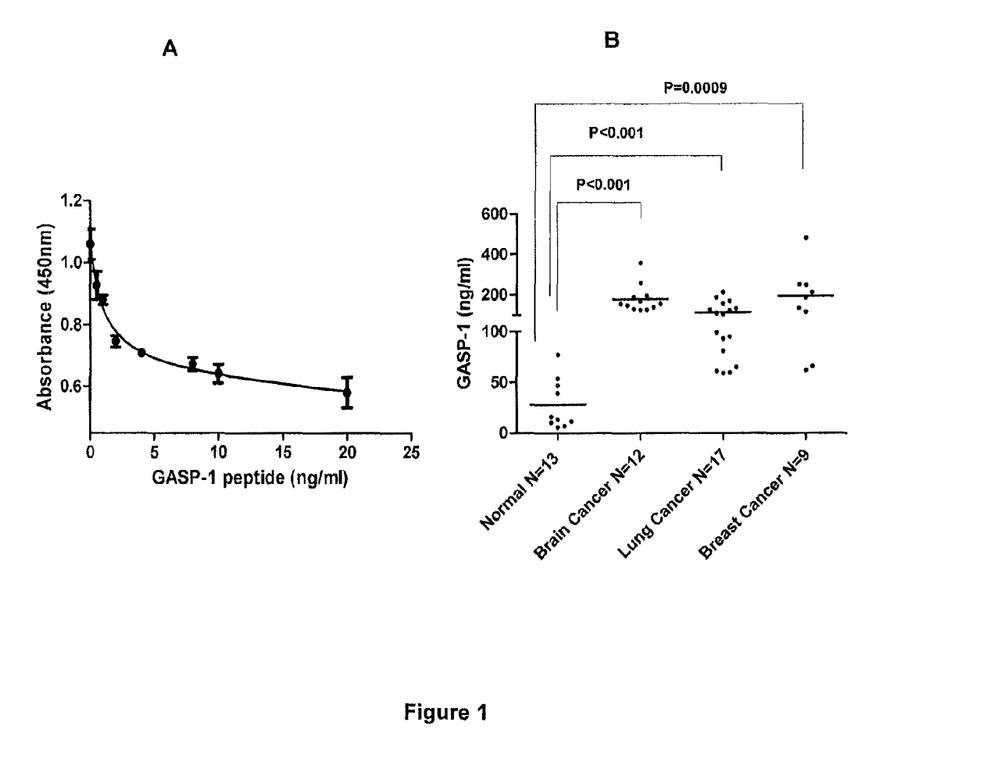
FIG. 1 illustrates elevated GASP-1 peptide levels in sera of patients with brain, lung and breast cancer as compared to those with no cancer. Panel A shows a "Competitive ELISA" standard curve obtained by least squares analysis of the data fitted as a one site-total binding curve using GraphPad Prism version 5.01 (San Diego, Calif.). Panel B shows a scatterplot of the data. Unknown values were extrapolated from the standard curve. P values were calculated by comparison of the groups using an unpaired t-test.

Due to the fact that the present invention preferably deals with very short peptide fragments (e.g., between about 6 to about 30 amino acids, between about 10 to about 25 amino acids, or between about 15 to about 20 amino acids), it will generally not be possible to produce two antibodies recognizing different regions of a small peptide fragment, such as the 16 amino acid peptide sequence described above. A new "Competitive ELISA" was invented that functions by equilibrium partitioning of biotinylated-anti-GASP-1 peptide antibody between GASP-1 peptide present in the serum with peptide absorbed in the wells of a microtiter plate. The more GASP-1 present in the serum, the less antibody is bound to the plate. Labeled antibody adsorbed on the bottom of the plate is then detected by HRP-streptavidin and the colorimetric substrate tetramethylbenzidine (TMB). FIG. 1 (panel A) shows a representative standard for detecting GASP-1 or GASP-1 peptide fragment. Competitive ELISAs of the present invention are highly sensitive and can detect less than 1 nanogram/ml GASP-1 peptide fragment levels in cancer patient sera. Because this "competitive ELISA" is so sensitive, it can measure the presence of a minute quantity of GASP-1 peptide fragment in blood.

It should be pointed out that because a polyclonal antibody is raised against the short (or even unique) peptide fragments and not to the whole protein, it will be very specific and not cross react with other protein in the body. It is expected when used as therapeutics; the peptide antibodies will be more specific and produce much less side effects, if any.

Alternative methods of the present invention comprise detecting an amount of GASP-1 nucleic acids present in a biological sample of the subject. For example, the nucleic acids may comprise GASP-1 mRNA or GASP-1 cDNA. GASP-1 mRNA can be detected by RT-qPCR or qPCR and GASP-1 cDNA can be detected by Immuno-PCR (IPCR). According to particular embodiments, the amount of GASP-1 cDNA in the sample may be determined by microarray or PCR array.

The step of determining the amount of GASP-1 mRNA in a test sample may comprise exposing the test sample to a nucleic acid molecule which hybridizes to a GASP-1 mRNA under stringent conditions. For example, the methods may employ a probe of around 30 nucleotides or longer in 0.5 M $NaHPO_4$/7% SDS/1 mM EDTA at 65° C. The stringent conditions may comprise washing in 0.1% SDS/0.1×SSC at 68° C.

More preferably the step of determining the amount of GASP-1 mRNA in the test sample entails a specific amplification of the mRNA and then quantification of the amplified product e.g. via RT-qPCR or qPCR analysis. The expression level of GASP-1 mRNA may be compared to a control e.g. a human cancer, and a normal non-cancer individual; or a human cancer cell line, and a human non-cancer cell line.

In one aspect the invention provides another method for detecting cancer or diseases at early stage in a biological sample from an individual, the method comprising assessing the level of cDNA in a biological tissue sample using Immuno-PCR (IPCR).

The quantitative immuno-PCR (IPCR) technology combines the advantages of flexible and robust immunoassays with the exponential signal amplification power of PCR. The IPCR allows one to detect antigens using specific antibodies labeled with double-stranded DNA. The label is used for signal generation by quantitative PCR. Because of the efficiency of nucleic acid amplification, IPCR typically leads to a 10- to 1,000-fold increase in sensitivity compared to an analogous enzyme-amplified immunoassay. A standard protocol of IPCR assay to detect specific antigen using a sandwich immunoassay combined with real-time PCR readout is described here. The protocol includes initial immobilization of the antigen, and coupling of this antigen with antibody-DNA conjugates is then carried out. Following this, nucleotides, specific primers and a polymerase are added and the marker is amplified by PCR for signal generation. The number of PCR amplicons produced is proportional to the initial quantity of antigen to be detected. The use of IPCR assays enables the detection of rare biomarkers in complex biological samples that are poorly accessible by conventional immunoassays.

Because GASP-1 protein and GASP-1 peptide fragment levels increase during the progression of cancer, they can also be used to monitor the progression of cancer. Thus, in other aspects of the invention, expression of GASP-1 or peptide fragments thereof may be used as a biomarker for choosing or monitoring specific therapeutic regimens and chemotherapeutic combinations. An embodiment of the present invention provides a method for monitoring the progression of cancer in a subject comprising (i) detecting the expression level of GASP-1 in the subject at a first time point (e.g., by detecting an amount of GASP-1 peptide fragments, such as fragments comprising the sequence EEASPEAVAGVGFESK, present in a biological sample of the subject during early stage cancer), (ii) detecting the expression level of GASP-1 in the subject at one or more subsequent time points, and (iii) comparing the expression level of GASP-1 detected at the one or more subsequent time points with the expression level of GASP-1 detected at the first time point. For example, a higher expression level of GASP-1 detected in step (ii) compared to the expression level of GASP-1 detected in step (i) indicates progression of the cancer; and a lower expression level of GASP-1 detected in step (ii) compared to the expression level of GASP-1 detected in step (i) indicates regression of the cancer.

The effectiveness of a disease treatment (e.g., chemotherapy, radiation, or medication) may be monitored by comparing the expression levels of GASP-1 before, during, and/or after treatment regimens. For instance, the cancer may be determined as progressing if the expression level increases over time, whereas the cancer may not be progressing if the expression level remains constant or decreases with time. According to such embodiments, the first time point may comprise a time point before a treatment regimen has begun (or at the time a treatment regimen is initiated) and the one or more subsequent time points may comprise time points during the course of the treatment regimen and/or after the treatment regimen has ended. The methods described above may alternatively comprise comparing GASP-1 expression levels in a subject to predetermined reference data which correlate expression levels of GASP-1 with various stages of cancer, in order to determine the subject's stage of cancer. The methods may be used to monitor the risk of cancer and cancer progression in the patient over time. The methods may also be used for determining whether a therapeutic treatment should be continued, or for monitoring the efficacy of an anticancer therapy which the patient is undergoing.

The diagnostic, prognostic and other methods described herein may be performed by use of a kit. Thus, the invention provides a kit for assessing or aiding in any of the diagnostic or prognostic methods described above, e.g., for measuring the presence of or amount of GASP-1 or peptide fragments thereof in a sample. An embodiment of the present invention provides a kit for determining whether cancer (e.g., early stage cancer) is present in a subject comprising a binding agent selective for a GASP-1 peptide fragment or a GASP-1 nucleic acid. The binding agent is preferably an antibody and the antibody is preferably selective for a GASP-1 peptide fragment comprising or consisting of the sequence EEASPEAVAGVGFESK. In another aspect a test kit may comprise a nucleic acid molecule comprising at least 6 contiguous nucleotides of the GASP-1 nucleotide sequence. The kit is useful for detecting mRNA corresponding to the nucleic acid molecule in a biological sample of the subject.

The nucleic acid may be one which directly analyzes mRNA by Northern or other blot analyses, or one (e.g. a primer) which can be used in enzymatic amplification and analysis of mRNA. In either case the kit may comprise a control sample comprising cells or biological fluid selected from the group consisting of a human cancer, and a human non-cancer. The antibody may be one useful for fluorescence microscopy, Western blot analysis, fluorescence activated cell sorting, immunohistochemical or other immunoassay.

In the light of the disclosure herein it can be seen that inhibition of GASP-1, peptide fragments thereof or their interacting partners may be useful in the treatment of cancer.

The terms "treatment" or "therapy" where used herein refer to any administration of a inhibitor of GASP-1, peptide fragments thereof, or an antagonist that interferes with GASP-1 (or its peptide fragments) interaction with its partners in order to alleviate the severity of cancer in a subject, and may include treatment intended to cure the disease, provide relief from the symptoms of the disease, and/or to inhibit or arrest the development of the disease in an individual at risk for developing the disease or an individual having symptoms indicating the development of the disease in that individual. In one embodiment, a method for inhibiting cancer progression comprises contacting the tumor derived therefrom with a GASP-1 inhibitor or antagonist that interferes with GASP-1 (or its peptide fragments) interaction with their partners.

The following examples are provided to describe embodiments of the invention in greater detail and are intended to illustrate, not limit, the invention.

EXAMPLES

Example 1

Identification of Cancer Peptide Motif from GASP-1

As indicated earlier, serum albumin complexes from Stage I breast cancer were separated using 2-D HPLE. The protein complex spots were subjected to on-membrane digestion with trypsin and the tryptic peptides identified by liquid chromatography with tandem spectrometry sequencing of individual peptides (LC/MS/MS). Protein identities were determined from database searches of virtual tryptic peptide data bases or fragmentation spectra of tryptic peptides. The Wistar Proteomic Facility in Philadelphia has developed a tryptic digest procedure for analyzing proteins and their fragments present in serum albumin complexes on PVDF membrane. Analysis of one of the differentially expressed spots of cancer protein complexes by LC/MS/MS revealed the presence of a peptide fragment having a sequence of EEASPEAVAGVG-FESK (SEQ ID NO: 1). This sequence matched 100% with G-protein coupled receptor-associated sorting protein 1 (GASP-1). GASP-1 (Reference #: Q5JY77) has 1,395 amino acids with a molecular weight of 156,865. The peptide identified comprises amino residues 850 to 865 of this GASP-1 protein.

Example 2

Development of "Competitive ELISA" for Quantification of GASP-1 and its Peptide Fragments in Patient Serum As indicated earlier, over-expression of GASP-1 in cancer tissues leads to the secretion and accumulation of a specific fragment containing 16-amino acid sequence (EEASPEAV-AGVGFESK (SEQ ID NO: 1)) of this protein into the blood. The GASP-1 fragment constitutes only about 1% of the entire protein and its amino acid sequence is unique because no other human proteins contain this particular sequence. It will be highly desirable to detect this or other peptide sequences from the over-expressed GASP-1 protein. A protocol for a "Competitive ELISA" according to the present invention, using a single antibody against GASP-1 peptide fragment, is provided below.

Experiments were carried out in triplicates. Two strip frames for inserting appropriate number of wells were prepared and name "plate A" and "plate B". Wells for both standards and samples on plate A were coated overnight with 300 ul of 1% bovine serum albumin (BSA) in PBS (pH7.4), at 4° C. Wells for both standards and samples on plate B were coated with 200 ul of peptide solution containing 100 ng of peptide in sodium carbonate buffer (pH 9.6), overnight at 4° C.

110 ul of standard solution ranging from 1, 2, 4, 6, 8, 16, 20, and 40 ng/ml and sample solutions to be analyzed were added to the BSA-coated plates. Both the samples and standards were in TSBT high salt (Tris-buffered saline with 0.05% Tween-20 and 0.5 M NaCl). After incubating for 30 min at room temperature, 110 ul of biotinylated anti-GASP-1 antibody (purified by A/G resin, Pierce Chemical. Rockford, Ill. USA) was added. The antibody was diluted 1:100 000 (1 ul antibody+99 ul TBST-High salt, take 20 ul and dilute into 20 ml TBST high salt.). After addition of the antibody solution, the final concentrations of standard solution become 0.5, 1, 2, 3, 4, 8, 10 and 20 ng/ml. The wells were shaken overnight at 4° C.

The next day, the unoccupied space from the peptide coated wells was blocked by coating them with 1% BSA by shaking at room temperature for 30 min. The wells were washed 5 times in 300 ul TBST high salt. 200 ul of antigen-antibody mixture from the BSA coated plate was transferred to peptide coated plate and shaking at room temperature for 1.5 h. This is followed by washing with 300 ul TBST high salt 5 times. Streptavidin-HRP (1:54000 dilution in TBST high salt) was then added to the well (200 ul/well). After shaking at room temperature for 1 h, the wells were washed with 300 ul TBST high salt 5 times. This was followed by adding 100 ul TMB (tetramethylbenzidine, Pierce Chemical, Rockford. Ill. USA). The wells were shaken at room temperature until O.D. 450 of TBST control (0 ng/ml in the standard curve) reaches 1.0. 1M HCl (50 ul/well) was then added to the wells to stop the reaction. After reading at O.D.450, Prism 5.0 was used to generate the standard curve (one site-total function) and to calculate GASP-1 concentrations of unknown samples. FIG. 1 (panel A) shows a representative standard for detecting GASP-1 or GASP-1 peptide fragment. The competitive ELISA is highly sensitive and can detect less than 1 nanogram/ml GASP-1 peptide levels in cancer patient sera. Because this "Competitive ELISA" is so sensitive it can measure the presence of a minute quantity of GASP-1 peptide fragments in blood.

Example 3

GASP-1 Peptide Levels are Elevated in Sera of Patients with Brain, Lung and Breast Cancer as Compared to Those with No Cancer Based on the standard curve, we determined GASP-1 levels in normal healthy individuals and patients with brain, lung and breast cancers (FIG. 1, panel B). Using our "Competitive ELISA" procedure, we found that sera from patients with brain, lung and lung cancer expressed 10-fold more GASP-1 peptide than sera from normal healthy individuals. It is evident that our ELISA can be used to detect the presence of these cancers.

Example 4

GASP-1 Peptide Levels are Elevated in Sera of Patients with Liver Cancer but not Liver Cirrhosis The over-expression of GASP-1 and the release of its peptide fragments appear to be specific for cancer development.

Figure 2:
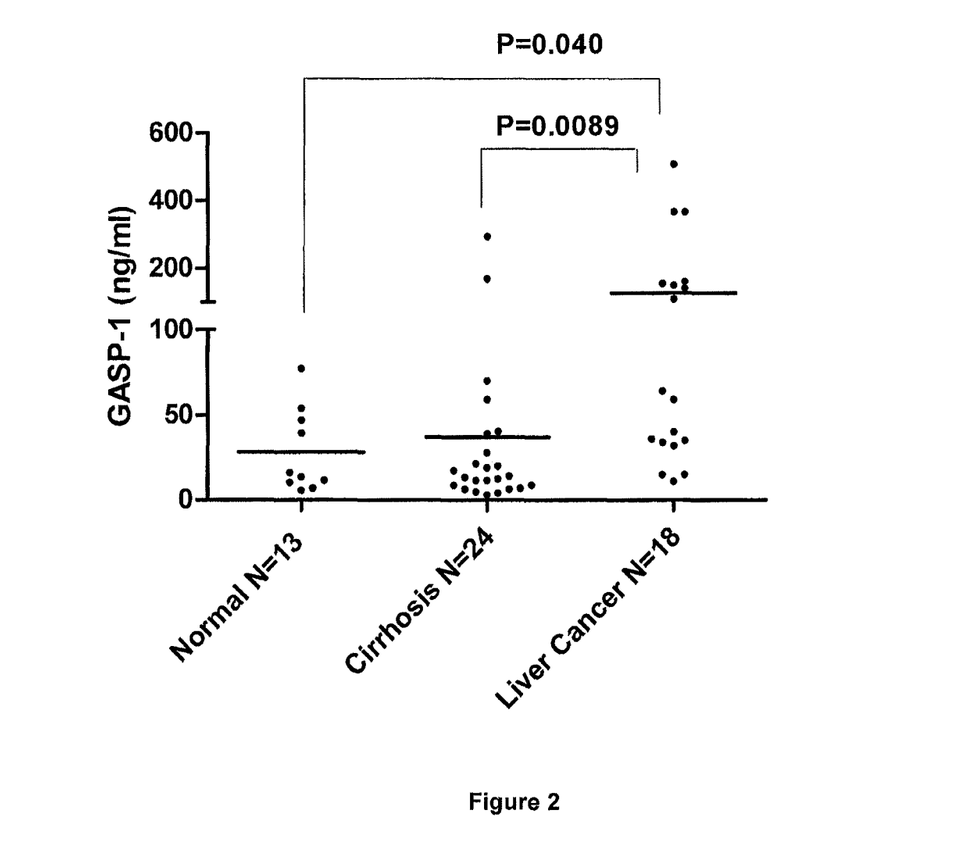
FIG. 2 illustrates elevated GASP-1 peptide levels in sera of patients with liver cancer as compared to those with no cancer or cirrhosis.

FIG. 2 shows that while the levels of GASP-1 peptide fragment in liver cancer are very high, the levels of GASP-1 peptide fragment in liver cirrhosis (a liver disease) are almost the same as those in the normal individuals. This finding suggests that over-expression of GASP-1 may be specific for cancers.

Example 5

Examples of GASP-1 Stained Tumors and their Respective Normal Tissue

The over-expression of GASP-1 in cancer tissues was confirmed by an immunohistochemical analysis of normal and cancerous tissues. We stained several cancer arrays purchased from US Biomax using the GASP-1 peptide antibody. These were breast cancer arrays BR1003 and BR1503, pancreatic cancer array PA2081, brain cancer array BS17016, colon cancer array TP242 and liver cancer array T032. The level of GASP-1 staining in the arrays was evaluated in a blinded fashion by Dr. Xinmin Zhang, Associate Professor of Pathology and Laboratory Medicine at Temple University. He scored the cases on a scale of 0 to 3, with 1 showing low, 2 showing moderate and 3 showing high staining intensity. We found that GASP-1 is highly over-expressed in brain, breast, colon, liver, lung, pancreatic, prostate cancers when compared to their respective normal tissues as assessed by immunohistochemical staining of tissue arrays using this peptide specific GASP-1 antibody. We found that across all cancers we studied, GASP-1 was expressed at 6 to 8 fold more in the cancer when compared to normal tissue.

Example 6

Figure 3:
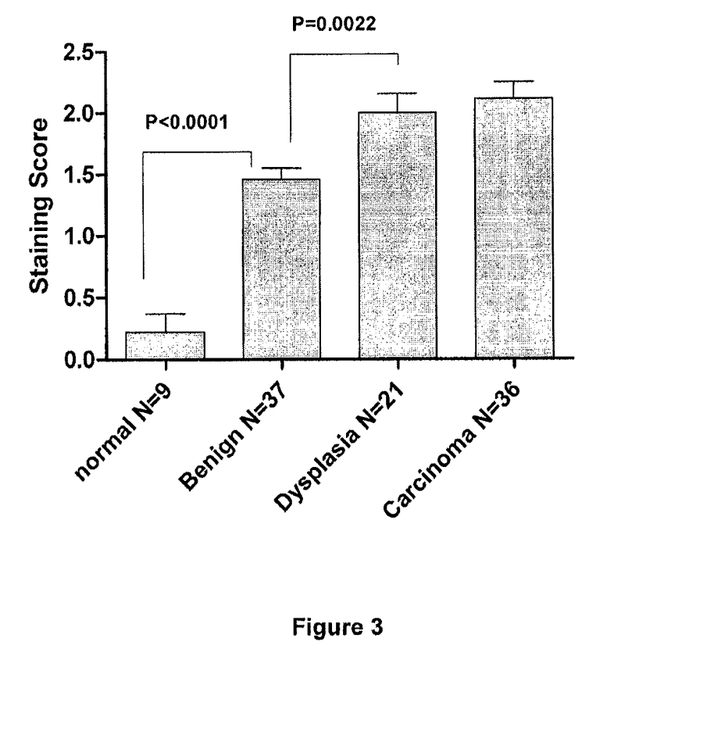
FIG. 3 illustrates significantly elevated GASP-1 in benign, pre-cancerous breast lesions, and breast tumors as compared to normal tissue. Breast cancer arrays BR1003 and BR1503 (US Biomax) were stained for GASP-1 as described in Tuszynski et al., 2011, and the staining intensity evaluated by a pathologist in a blinded fashion.

GASP-1 is Significantly Elevated in Benign, Pre-Cancerous Breast Lesions, and Breast Tumors as Compared to Normal Tissue Using GASP-1 peptide antibody, we immunohistochemically stained 37 cases of benign precancerous (i.e., early stage cancer), 21 cases of dysplasia (i.e., early stage cancer) and 36 cases of carcinoma (breast cancer with detectable symptoms). The level of GASP-1 staining in the arrays was evaluated in a blinded fashion by Dr. Xinmin Zhang. Interestingly, we observed a wide spectrum of enhanced staining of premalignant ductal epithelial cells present in benign ducts. There is a 4 to 6-fold over-expression of GASP-1 in these benign ducts (FIG. 3). A 6 to 8-fold increase in GASP-1 expression was seen in dysplasia (early stage cancer) as compared to normal tissue (FIG. 3). These findings suggest that the over-expression of GASP-1 occurs very early in cancer development before symptoms appear.

Example 7

GASP-1 is Highly Expressed in Triple-Negative Breast Cancer as Well in Early Stage Breast Cancers such as Ductal Carcinoma in Situ (DCIS) and Hyper-Proliferative Lesions Such as Atypical Ductal Hyperplasia (ADH)

Figure 4:
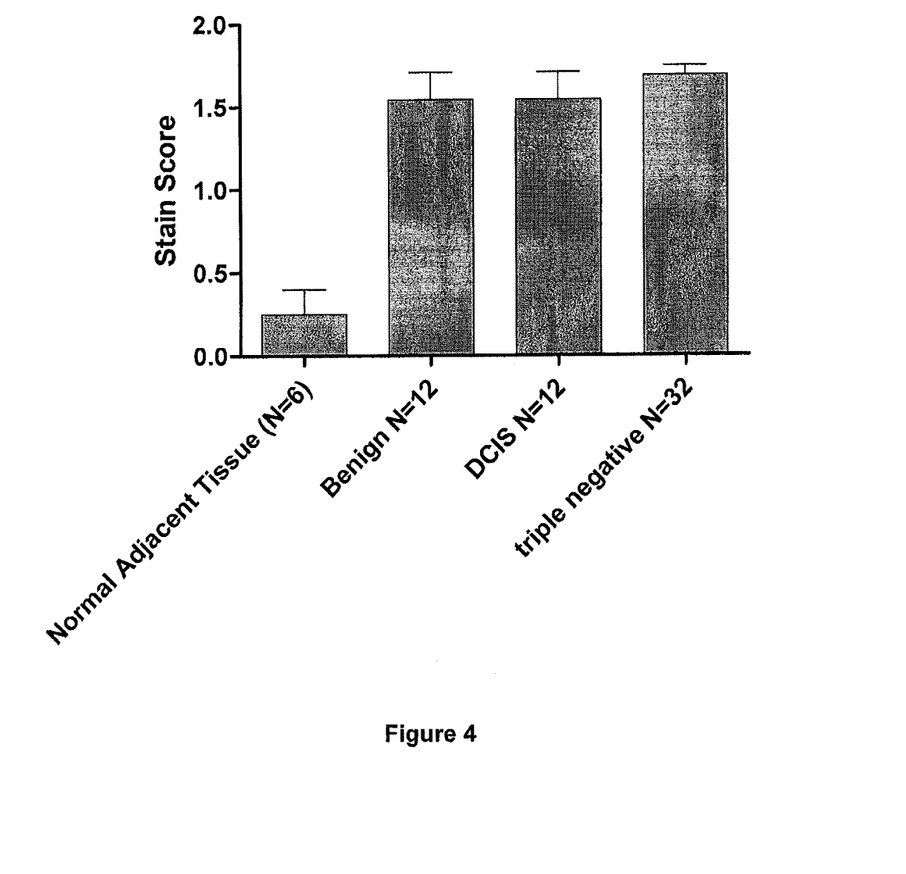
FIG. 4 shows that GASP-1 is highly expressed in Triple Negative Breast Cancer as well as in early stage breast cancers such as ductal carcinoma in situ (DCIS). Breast cancer array BR1503 (US Biomax) was stained for GASP-1 as described in Tuszynski, G. P., et al., 2011. The staining intensity was evaluated by a pathologist in a blinded fashion.

Currently, no biomarkers for triple negatives have been found. FIG. 4 shows that when compared to the adjacent normal tissues, there is about 6-fold increase in GASP-1 staining in triple-negative breast cancer by immunohistochemical staining of tissue arrays using this peptide specific GASP-1 antibody. This finding suggests that GASP-1 is a potential new tumor biomarker for triple-negative breast cancer. A similar increase in other breast cancer (ADH/DCIS and carcinomas) was also observed. Our results further suggest that GASP-1 represents a new target for breast cancer therapy. Antagonizing the receptor recycling activity of GASP-1 could block important breast cancer GPCR's such as GPCR30, which have been shown to positively impact breast cancer progression (Thomas et al., 2006; Filardo et al., 2007).

Example 8

Figure 5:
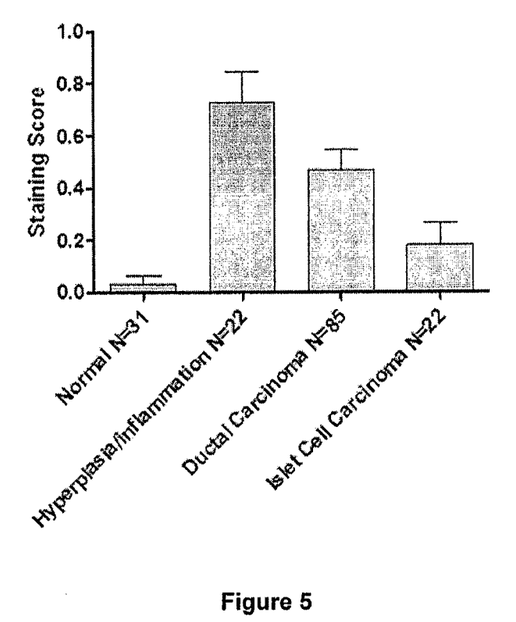
FIG. 5 illustrates the over-expression of GASP-1 in pancreatic cancer and hyperplastic and inflammatory lesions of the pancreas as compared to normal pancreas. Pancreatic cancer array PA2081 (US Biomax) was stained for GASP-1 as described in Tuszynski et al., 2011, and the staining intensity evaluated by a pathologist in a blinded fashion.

GASP-1 is Over-Expressed in Pancreatic Cancer and Hyperplastic and Inflammatory Lesions of the Pancreas as Compared to Normal Pancreas In pancreatic cancer, there was a statistically significant difference in the staining of normal pancreatic tissue which showed little or no staining as compared to the pancreatic carcinoma groups and hyperplastic (early stage cancer) and inflammatory pancreatic disease (which is associated with cancer progression). FIG. 5 shows that in pancreatic cancer an increase in GASP-1 expression was seen in hyperplastic and inflammatory lesions as compared to normal tissue.

Example 9

Cancer Cell Growth is Dependent on GASP-1

Figure 6:
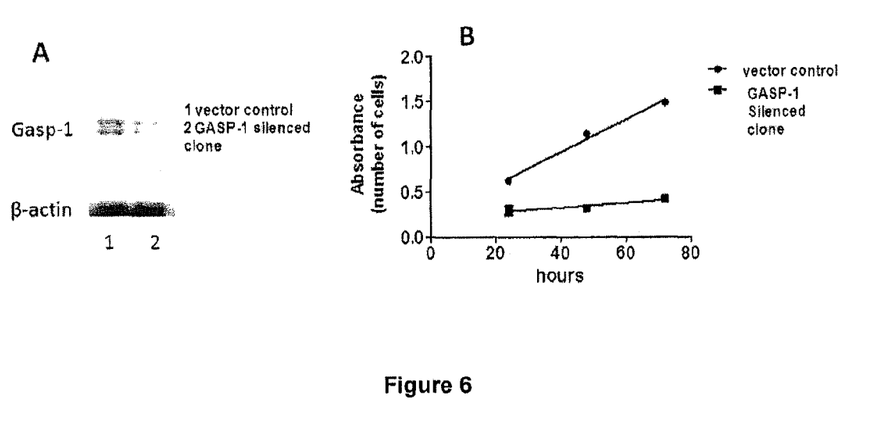
FIG. 6 illustrates the effects of GASP-1 silencing with GASP-1 shRNA on MB-231 cell growth. In Panel A, a Western blot using anti-GASP-1 antibody of MB-231 cells shows that cells transfected with a single shRNA construct exhibit wild-type expression of GASP-1, while cells transfected with all four constructs together show approximately 90% reduction in GASP-1 expression. Panel B shows that GASP-1 silencing results in approximately 10-fold reduction in MB-231 cell growth.

To validate that GASP-1 is a biomarker of cancer pathoetiology, and a potential therapeutic target, the effect of GASP-1 gene silencing was evaluated in a prototypical breast cancer cell line. The MB-231 cell line is an example of a highly invasive estrogen receptor negative metastatic breast cancer cell line. Four GASP-1-specific shRNA expression vectors in pGFP-V-RS plasmid were constructed by Origene using complimentary RNA sequences of GASP-1 that would be expected to have high hybridization activity with the coding sequences of GASP-1. Each was transfected separately, and all in combination, into cells according to the manufacturer's instructions. Additionally, cells were transfected with negative-control plasmids which contained either RNA from a non-coding region of GASP-1, scrambled RNA, or no RNA. Cells were selected in media containing 1 µg/ml puromycin. Cells were evaluated for growth over 72 hours following transfection, and then prepared for Western Blot using an anti-GASP-1 antibody. Cells transfected with all four shRNA constructs exhibited substantially (90%) lower GASP-1 expression compared with negative controls and cells transfected with any single construct (FIG. 6, panel A). The growth rate of these GASP-1 repressed cells was ten-fold slower than controls (FIG. 6, panel B). These results indicate that GASP-1 promotes MB-231 cell proliferation and plays an important role in breast cancer progression. It is likely that other metastatic breast cancer cell lines will also use GASP-1 to mediate their proliferation, particularly in view of the fact that all the patient ductal breast tumors we have examined expressed high levels of GASP-1.

The fact that cancer cell growth is dependent upon the over-expression of the GASP-1 gene suggests the possibility of using the over-expression of either GASP-1 mRNA or cDNA as a surrogate biomarker for cancer detection.

REFERENCES

Ariazi E A, Ariazi J L, Cordera F, Jordan V C. Estrogen receptors as therapeutic targets in breast cancer. (2006) *Current Topics in Medicinal Chemistry* 6(3):181-202.

Barton C L (2006) Commercial opportunities from biomarkers transforming drug discovery, clinical development and molecular diagnostic. London, UK: Business Insights Ltd.

Baselga J. Targeting tyrosine kinases in cancer: The second wave. (2006) *Science* 312(5777): 1175-1178.

Chang F N, Yonan C R. System and methods for electrophoretic separation of proteins on protein binding membranes. (2008) U.S. Pat. No. 7,326,326.

Chang F N, Duong P, Tuszynski, G P (2009) Method for detecting disease markers. WO/2009/014552.

Corthals G L, Wasinger V C, Hochstrasser D F, Sanchez J C: The dynamic range of protein expression: A challenge for proteomic research. (2000) *Electrophoresis* 21:1104-1115.

Dennis M S, et al. Albumin binding as a general strategy for improving the pharmacokinetics of proteins. (2002) *J. Biol. Chem.* 277: 35035-43.

Druker B J. Imatinib as a paradigm of targeted therapies. (2004) *Advances in Cancer Research* 91:1-30.

Duffy M J. Predictive markers in breast and other cancers: A review. (2005) *Clinical Chemistry* 51(3):494-503.

Filardo E, Quinn J, Pang Y, Graeber C, Shaw S, Dong J, Thomas P. Activation of the novel estrogen receptor G Protein-coupled receptor 30 (GPR30) at the plasma membrane. (2007) *Endocrinology* 148:3236-3245

Gasparini G, Longo R, Torino F, Gattuso D, Morabito A, Toffoli G. Is tailored therapy feasible in oncology? (2006) *Critical Reviews in Oncology/Hematology* 57(1):79-101.

Merrell K, Southwick K, Graves S W, Esplin M S, Lewis N E, Thulin C D: Analysis of low-abundance, low-molecular-weight serum proteins using mass spectrometry. (2004) *J. Biomol. Tech.* 15:238-248.

Moser E., Kargl J, et al. G Protein-coupled receptor associated sorting protein-1 regulates the postendocytic sorting of seven-transmembrane-spanning G Protein-coupled receptors. (2010) *Pharmacology* 86:22-29.

O'Farrell, P H. High resolution two-dimensional electrophoresis of proteins. (1975) *J Biol Chem* 250: 4007-21.

Ryberg E., Larsson N. et al. The orphan receptor GPR55 is a novel cannabinoid receptor. *Brit. J Pharmacol.* 152(7): 1092-1101.

Simonin F, Karcher P, Boeuf J J, Matifas A, Kieffer B L. Identification of a novel family of G protein-coupled receptor associated sorting proteins. (2004) *J Neurochem.* 89: 766-775.

Thomas P, Dong J. Binding and activation of the seven-transmembrane estrogen receptor GPR30 by environmental estrogens: A potential novel mechanism of endocrine disruption. (2006) *J Steroid Biochem. and Mol. Biol.* 102: 175-179

Tuszynski, G P., et al., 2011. G-protein coupled receptor-associated sorting protein 1 (GASP-1), a potential biomarker in breast cancer. *Exp Mol Pathol.* 91, 608-13.

Whistler, J., Enquist J. et al. Modulation of postendocytic sorting of G Protein-coupled receptors. (2002). *Science* 297: 615-620.

Yeon C H, Pegram M D. Anti-erbB-2 antibody trastuzumab in the treatment of HER2-amplified breast cancer. (2005) *Investigational New Drugs* 23(5):391-409.

Although the present invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the appended claims.

---

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Completely Synthesized

<400> SEQUENCE: 1

Glu Glu Ala Ser Pro Glu Ala Val Ala Gly Val Gly Phe Glu Ser Lys
1               5                   10                  15
```

---

Hayes D F. Prognostic and predictive factors revisited. (2005) *Breast* 14(6):493-499.

He P, He H Z, Dai J, Wang Y, Sheng Q H, Zhou L P, Zhang Z S, Sun Y L, Liu F, Wang K, et al. The human plasma proteome: Analysis of Chinese serum using shotgun strategy. (2005) *Proteomics,* 5:3442-3453.

Lowenthal, M. S. et al. Analysis of albumin-associated peptide and proteins from ovarian cancer patients. (2005) *Clinical Chemistry* 51: 1933-45.

What is claimed is:

1. A method for treating early stage cancer in a subject comprising administering to the subject an effective amount of a peptide antibody to inhibit or arrest the progression of early stage cancer to late stage cancer, wherein said peptide antibody binds a cancer peptide motif that is amino acid sequence SEQ ID NO: 1.

2. The method of claim 1 comprising administering the peptide antibody in a pharmaceutically acceptable carrier.

3. The method of claim 1, wherein the early stage cancer is selected from the group consisting of a benign condition, hyperplasia, dysplasia, and carcinoma in situ.

4. The method of claim 1, wherein the early stage cancer is early stage breast cancer.

5. The method of claim 4, wherein the breast cancer is triple-negative breast cancer.

* * * * *